United States Patent [19]
Grunig et al.

[11] 3,966,909
[45] June 29, 1976

[54] SOLVENT EXTRACTION OF ALUMINUM

[75] Inventors: James K. Grunig; Rodney J. Anderson, both of Tucson, Ariz.

[73] Assignee: The Anaconda Company, New York, N.Y.

[22] Filed: Mar. 13, 1975

[21] Appl. No.: 558,149

Related U.S. Application Data

[63] Continuation-in-part of Ser. No. 444,004, Feb. 20, 1974, abandoned.

[52] U.S. Cl. ............................. 423/112; 75/101 BE
[51] Int. Cl.² ..................... B01D 11/04; G01F 7/00
[58] Field of Search ........................... 423/112, 139; 75/101 BE

[56] References Cited
UNITED STATES PATENTS

| | | | |
|---|---|---|---|
| 3,211,521 | 10/1965 | George et al. | 423/112 |
| 3,320,032 | 5/1967 | Feller | 423/112 |
| 3,514,266 | 5/1970 | Nichols et al. | 423/112 |
| 3,545,920 | 12/1970 | George et al. | 423/112 |
| 3,816,590 | 6/1974 | Huska et al. | 423/112 |

*Primary Examiner*—Herbert T. Carter
*Attorney, Agent, or Firm*—Pennie & Edmonds

[57] ABSTRACT

A process is described for the selective recovery of aluminum from an impure solution in which aluminum is dissolved, comprising contacting said solution with a symmetrical bis(3,5-$C_1$–$C_{10}$ alkyl-substituted phenyl) hydrogen phosphate to extract the aluminum, and separating the aluminum from said extract.

7 Claims, No Drawings

SOLVENT EXTRACTION OF ALUMINUM

CROSS-REFERENCE TO RELATED APPLICATION

The instant application is a continuation-in-part of application Ser. No. 444,004, filed Feb. 20, 1974, now abandoned.

BACKGROUND OF THE INVENTION

Significant amounts of aluminum may be recovered from clays and other low grade aluminum-bearing ores by acid leaching of the ore (for example, a clay which preferably has been calcined) to yield a solution containing soluble aluminum $Al^{+++}$ as the sulfate, the nitrate or the chloride. Such solution normally may also contain undesirable ions, and, in particular, iron as $Fe^{+++}$. Iron is most undesirable since its presence interferes with the economic production of high purity aluminum metal.

Prior art processes, typified by that disclosed in U.S. Pat. No. 3,211,521, teach the purification of liquids containing aluminum and iron ions by the process wherein an aqueous solution thereof is contacted with an alkyl-substituted phosphoric acid, $HRR'PO_4$ wherein R is a straight chain or branched chain alkyl radical containing at least 8 carbon atoms and R' is a hydrogen or alkyl. Typical of such compositions is dioctyl phosphoric acid. In use of such techniques, the alkyl-substituted phosphoric acid is contacted with aqueous liquor containing aluminum and iron; and the alkyl-substituted phosphoric acid will become loaded with iron without picking up any appreciable quantity of aluminum. The result is the aqueous liquor must still be further treated to separate the aluminum from the other undesired impurities. The result is extended processing which is costly in terms of time and capital equipment.

Efforts to use aryl-substitued phosphates are typified by U.S. Pat. No. 3,320,032 in which benzyl, naphthyl, and tolyl radicals are disclosed. However, none of these are selective for aluminum and, in fact, the entire disclosure of this patent is to use organic hydrogen phosphates to selectively extract iron from aluminum solutions; not to remove aluminum selectively from an impure solution.

SUMMARY OF THE INVENTION

This invention provides a novel process for permitting rapid, low cost recovery of aluminum from solutions containing other ions including iron.

Briefly stated, this invention comprises the process of extracting aluminum from an aqueous solution containing aluminum ions by:

a. contacting said aqueous solution in a contacting operation with a symmetrical bis(3,5-$C_1$-$C_{10}$alkyl-substituted phenyl) hydrogen phosphate to extract the alumina;

b. withdrawing from said contacting operation a lean aqueous solution substantially free of aluminum; and c. recovering said aluminum from said complex.

DETAILED DESCRIPTION

In accordance with certain aspects of this invention, the rich aqueous solution containing aluminum ions may, typically, be a solution obtained by leaching an aluminum-bearing ore, such as a calcined alumino-silicate clay, with a dilute mineral acid. The most common of such aluminum-bearing ores, such as kaolin and bauxite, may include various aluminum silicates, metal aluminates, aluminum oxides, and the like together with substantial amount of iron and silica and lesser amounts of other impurities.

The invention contemplates recovering aluminum from such ores (after calcining, in the case of clay) by leaching with an acidic leach liquor in which the acid is preferably sulfuric acid, although hydrochloric or nitric acid can also be used. The acid is present in an amount stoichiometrically adequate to dissolve the alumina ($Al_2O_3$) content of the calcined clay or other ore. The residue may be subject to further treatment, as by acidic washing, to recover any remaining solubilized aluminum.

Such calcining, leaching, and washing do not form a necessary part of the instant invention, for any conventional procedure which yields an impure aluminum containing solution can be utilized.

In accordance with the present invention, the aluminum-containing solution is treated with a symmetrical bis(3,5-$C_1$-$C_{10}$alkyl-substituted phenyl) hydrogen phosphate in the hydrogen form to extract the aluminum therefrom.

As used herein, the term "symmetrical bis(3,5-$C_1$-$C_{10}$akyl-substituted phenyl) hydrogen phosphate" refers to a phosphate having the structural formula

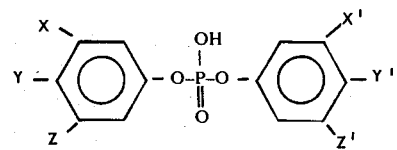

wherein each of X and Z is a $C_1$-$C_{10}$ alkyl group, Y is selected from hydrogen and $C_1$-$C_5$ alkyl group, X', Y', and Z' correspond, respectively, to X, Y, and Z, and when Y and Y' are greater than $C_1$, X, X', Z and Z' are at least 3 carbon atoms longer in chain length.

Specific examples of suitable phosphates are bis(3,5-dimethylphenyl) hydrogen phosphate, bis(3,4,5-trimethylphenyl) hydrogen phosphate, bis(3-ethyl-5-methylphenyl) hydrogen phosphate, bis(3,5 dihexylphenyl) hydrogen phosphate, 4 bis(3,5 decylphenyl) hydrogen phosphate, bis(3-decyl-4-ethyl-5-decylphenyl) hydrogen phosphate, bis(3,5 dibutylphenyl) hydrogen phosphate, and the like. The bis(3,5-dimethylphenyl) hydrogen phosphate is preferred because of its greater selectivity for aluminum.

The phosphate preferably is used as a liquid ion exchanger by dissolving it in a water-immiscible organic solvent such as commercial kerosene, octane, heptane, toluene, xylene, or the like. Solubility of the phosphate in such hydrocarbons may be enhanced by the use of an alkanol cosolvent, which advantageously is a $C_6$ to $C_{12}$ alkanol such as hexyl, heptyl, octyl, monyl, decyl, or dodecyl alcohol.

As to proportions, for each 100 parts by weight of aluminum contained in the leach solution there is used from about 3000 part by weight of bis(3,5-dimethylphenyl) hydrogen phosphate. Alkyl substituted aryl hydrogen phosphates of different molecular weight will require proportionately different amounts.

In carrying out the extraction, any conventional cocurrent or countercurrent scrubbing or contact apparatus now used for liquid ion extractions can be used to ensure that the organic phosphate solution and the aqueous acidic aluminum-containing solution are thoroughly admixed.

The pH of the aqueous phase is that of the leach solution at the conclusion of the acid leach operation; i.e., about 1 to about 3.5; and, while ambient temperature and pressure is preferred during extraction, slightly elevated temperatures and pressures are also suitable.

During this extraction, the phosphate becomes loaded with aluminum and with some iron, while the aqueous leach solution is depleted in aluminum. Substantially all other undesired impurities, save for the co-extracted iron, remain in solution.

The loaded phosphate extract is then stripped to remove the aluminum therefrom. Preferably, stripping is effected by contact of the loaded organic phase with an aqueous phase containing acid at a substantially higher strength than that of the leach solution entering the extraction stage. Typical of such acids may be hydrochloric acid, nitric acid, sulfuric acid, and the like, with hydrochloric acid being preferred; and the strength of the acid solution delivered to the stripping stage in general is advantageously equivalent to a nearly saturated aluminum salt solution at the temperature of operation. Thus, a 28% hydrochloric acid solution is equivalent, after the hydrogen-aluminum exchange, to a saturated aluminum chloride solution. However, somewhat lower strength acids may be used; for example, 20% hydrochloric acid may be used as the stripping acid.

The organic solution recovered from the stripping operation contains the regenerated acid form of the phosphate and can be recycled for use in further extraction; and the aqueous phase from the stripping operation contains an iron-contaminated aluminum chloride.

The aqueous aluminum chloride solution may be preferably treated in an iron-extraction operation, wherein the iron is removed from the solution by contacting with a tertiary amine or quaternary ammonium salt of the type now used for iron extraction. A substantially pure aluminum salt, or alumina, may be recovered by known procedures from the resulting iron-free aqueous strip solution.

While the invention has been described in connection with a preferred embodiment, it is not intended to limit the invention to the particular form set forth, but, on the contrary, it is intended to cover such alternatives, modifications and equivalents as may be included within the spirit and scope of the invention as defined by the appended claims.

What is claimed is:

1. A process for recovering aluminum from an impure acidic solution containing aluminum and iron comprising contacting the said solution with a symmetrical bis(3,5-$C_1$-$C_{10}$ alkyl-substituted pheny) hydrogen phosphate to extract the aluminum and stripping the extract to separate the aluminum from the extract formed, said phosphate having the structural formula:

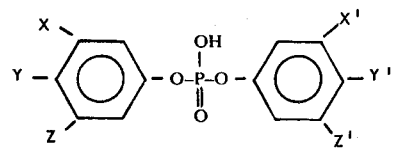

wherein each of X and Z is a $C_1$-$C_{10}$ alkyl group, Y is selected from hydrogen and a $C_1$-$C_5$ alkyl group, X', Y', and Z' correspond, respectively, to X, Y, and Z, and when Y and Y' are greater than $C_1$, X, X', Z and Z' are at least 3 carbon atoms longer in chain length.

2. The process of claim 1 wherein said phosphate is bis(3,5-dimethylphenyl) hydrogen phosphate.

3. The process of claim 1 wherein said extraction is carried out by contacting the impure aluminum-containing solution with a solution of the phosphate in a hydrocarbon solvent.

4. The process of claim 3 wherein the hydrocarbon solvent is kerosene.

5. The process of claim 3 wherein the solubility of the phosphate in the hydrocarbon solvent is enhanced by the presence therein of a $C_6$ to $C_{12}$ alkanol cosolvent.

6. The process of claim 1 wherein the aluminum is separated from the phosphate at the conclusion of the extraction operation by contacting the phosphate extract with an aqueous mineral acid solution at a pH lower than that of the impure acidic solution delivered to the extraction operation.

7. The process of claim 1 wherein said phosphate is bis(3,5-dimethylphenyl) hydrogen phosphate, the extraction is carried out with a solution of said phosphate in a solvent comprising kerosene and a $C_6$ to $C_{12}$ alkanol, and the aluminum is separated from the phosphate at the conclusion of the extraction operation by contacting the phosphate extract with an aqueous mineral acid solution at a pH lower than that of the impure acidic solution delivered to the extraction operation.

* * * * *